US012658322B2

(12) United States Patent
Hammond et al.

(10) Patent No.: US 12,658,322 B2
(45) Date of Patent: Jun. 16, 2026

(54) METHODS AND SYSTEMS FOR PROVIDING DIAGNOSIS ASSISTANCE USING SIMILARITY SEARCH BI-DIRECTIONAL COMMUNICATIONS TO RESOLVE INDETERMINATE DIAGNOSES

(71) Applicant: IDEXX Laboratories, Inc., Westbrook, ME (US)

(72) Inventors: Jeremy Hammond, Westbrook, ME (US); Patrick Doyle, Old Orchard Beach, ME (US)

(73) Assignee: IDEXX LABORATORIES, INC., Westbrook, ME (US)

( * ) Notice: Subject to any disclaimer, the term of this patent is extended or adjusted under 35 U.S.C. 154(b) by 180 days.

(21) Appl. No.: 18/396,207

(22) Filed: Dec. 26, 2023

(65) Prior Publication Data

US 2024/0221944 A1     Jul. 4, 2024

Related U.S. Application Data

(60) Provisional application No. 63/435,944, filed on Dec. 29, 2022.

(51) Int. Cl.
*G16H 50/20*         (2018.01)
*G16H 10/60*         (2018.01)

(52) U.S. Cl.
CPC ............. *G16H 50/20* (2018.01); *G16H 10/60* (2018.01)

(58) Field of Classification Search
CPC ........ G16H 50/20; G16H 10/60; G16H 50/70; G16H 10/40
See application file for complete search history.

(56)                References Cited

U.S. PATENT DOCUMENTS

2019/0183429 A1*  6/2019  Sung .................... A61B 5/7267
2021/0090694 A1*  3/2021  Colley ................... G16H 50/50
(Continued)

FOREIGN PATENT DOCUMENTS

WO       2022/120256       6/2002
WO    WO-2020183365 A1 *  9/2020   ............. G16H 50/70

OTHER PUBLICATIONS

Srinivasu PN, Shafi J, Krishna TB, Sujatha CN, Praveen SP, Ijaz MF. Using Recurrent Neural Networks for Predicting Type-2 Diabetes from Genomic and Tabular Data. Diagnostics (Basel). Dec. 6, 2022;12(12):3067. doi: 10.3390/diagnostics12123067. PMID: 36553074; PMCID: PMC9776641. (Year: 2022).*
(Continued)

*Primary Examiner* — Sun M Li
(74) *Attorney, Agent, or Firm* — McDonnell Boehnen Hulbert & Berghoff LLP

(57)                ABSTRACT

An example computer-implemented method for providing diagnosis assistance includes receiving initial data associated with a diagnostic test result of a subject, selecting from among a plurality of machine-learning logic a machine-learning logic for execution based on a type of the diagnostic test result, determining by executing the machine-learning logic and based on the initial data a similarity between the initial data and diagnostic test result data stored in a database, based on the similarity between the initial data and the diagnostic test result data being within a similarity threshold providing an inquiry for display at the remote computing device to solicit additional information useful to resolve the undetermined outlier, receiving input data from the remote computing device in response to the inquiry, and storing the input data in the database.

21 Claims, 7 Drawing Sheets

(56)        References Cited

U.S. PATENT DOCUMENTS

| | | | |
|---|---|---|---|
| 2021/0117729 A1* | 4/2021 | Bharti | G01N 15/1429 |
| 2022/0020505 A1* | 1/2022 | Pulitzer | G06Q 10/10 |
| 2022/0254458 A1* | 8/2022 | Mooney | G16H 50/20 |
| 2023/0120282 A1* | 4/2023 | Purushothaman | G06N 3/08 |
| | | | 705/2 |
| 2023/0154215 A1* | 5/2023 | Bharti | G06V 20/69 |
| | | | 382/133 |
| 2023/0260665 A1* | 8/2023 | Swisher | G16H 50/70 |
| | | | 705/2 |

OTHER PUBLICATIONS

Martin-Isla C, Campello VM, Izquierdo C, Raisi-Estabragh Z, Baeßler B, Petersen SE, Lekadir K. Image-Based Cardiac Diagnosis With Machine Learning: A Review. Front Cardiovasc Med. Jan. 24, 2020;7:1. doi: 10.3389/fcvm.2020.00001. PMID: 32039241; PMCID: PMC6992607. (Year: 2020).*

Fan, K., et al.; "A Machine Learning Assisted, Label-free, Non-invasive Approach for Somac Reprogramming in Induced Pluripotent Stem Cell Colony Formaon Detecon and Predicon", Scientific Reports, vol. 7, No. 1, Oct. 18, 2017 (Oct. 18, 2017), XP055505954, DOI: 10.1038/s41598-017-13680-x. (Year: 2017).*

S. M. Hosseini, M. Babaie and H. R. Tizhoosh, "Learning Similarity via Subjective Evaluations and Deep Features of Histopathology Images, " 2021 IEEE 21st International Conference on Bioinformatics and Bioengineering (BIBE), Kragujevac, Serbia, 2021, pp. 1-5, doi: 10.1109/BIBE52308.2021.9635177. (Year: 2021).*

C. Comito, D. Falcone and A. Forestiero, "AI-Driven Clinical Decision Support: Enhancing Disease Diagnosis Exploiting Patients Similarity," in IEEE Access, vol. 10, pp. 6878-6888, 2022, doi: 10.1109/ACCESS.2022.3142100. (Year: 2022).*

International Search Report and Written Opinion prepared by the European Patent Office in international application No. PCT/US23/085911 dated May 13, 2024.

* cited by examiner

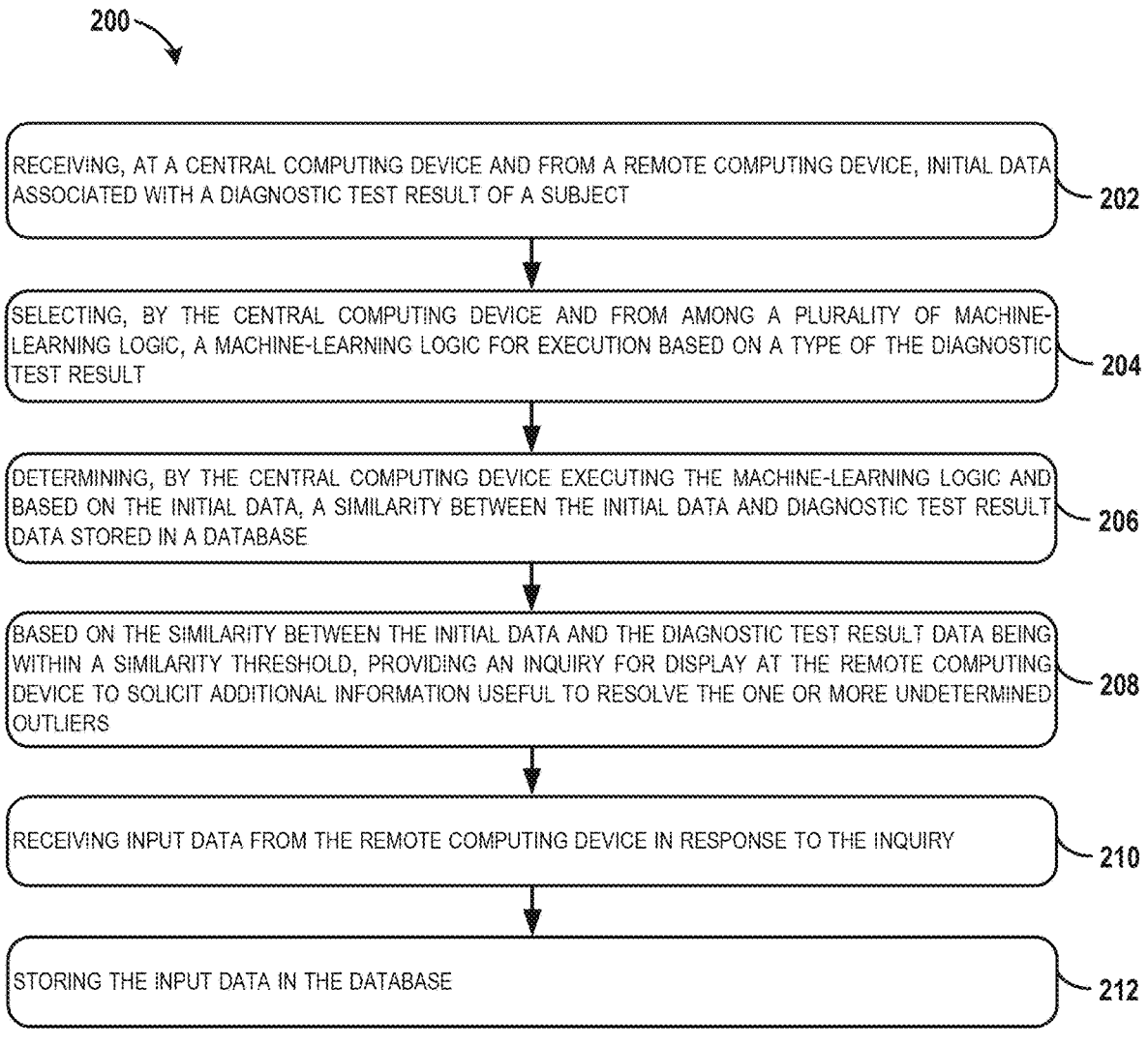

200

RECEIVING, AT A CENTRAL COMPUTING DEVICE AND FROM A REMOTE COMPUTING DEVICE, INITIAL DATA ASSOCIATED WITH A DIAGNOSTIC TEST RESULT OF A SUBJECT — 202

SELECTING, BY THE CENTRAL COMPUTING DEVICE AND FROM AMONG A PLURALITY OF MACHINE-LEARNING LOGIC, A MACHINE-LEARNING LOGIC FOR EXECUTION BASED ON A TYPE OF THE DIAGNOSTIC TEST RESULT — 204

DETERMINING, BY THE CENTRAL COMPUTING DEVICE EXECUTING THE MACHINE-LEARNING LOGIC AND BASED ON THE INITIAL DATA, A SIMILARITY BETWEEN THE INITIAL DATA AND DIAGNOSTIC TEST RESULT DATA STORED IN A DATABASE — 206

BASED ON THE SIMILARITY BETWEEN THE INITIAL DATA AND THE DIAGNOSTIC TEST RESULT DATA BEING WITHIN A SIMILARITY THRESHOLD, PROVIDING AN INQUIRY FOR DISPLAY AT THE REMOTE COMPUTING DEVICE TO SOLICIT ADDITIONAL INFORMATION USEFUL TO RESOLVE THE ONE OR MORE UNDETERMINED OUTLIERS — 208

RECEIVING INPUT DATA FROM THE REMOTE COMPUTING DEVICE IN RESPONSE TO THE INQUIRY — 210

STORING THE INPUT DATA IN THE DATABASE — 212

FIG. 7

METHODS AND SYSTEMS FOR PROVIDING DIAGNOSIS ASSISTANCE USING SIMILARITY SEARCH BI-DIRECTIONAL COMMUNICATIONS TO RESOLVE INDETERMINATE DIAGNOSES

CROSS REFERENCE TO RELATED APPLICATION

The present disclosure claims priority to U.S. provisional application No. 63/435,944, filed on Dec. 29, 2022, the entire contents of which are herein incorporated by reference.

FIELD

The present disclosure relates generally to methods and systems for providing diagnosis assistance, and more particularly to executing machine-learning logic to determine a similarity between initial input data and diagnostic test result data stored in a database to generate an inquiry to solicit additional information useful to resolve an undetermined outlier.

BACKGROUND

A challenge scientists and engineers face when developing new diagnostic instrumentation or improving existing devices is outlier analysis, such as when results do not fall within expected or known outcomes. Identifying, qualifying, determining root causes, and implementing solutions to unexpected outcomes can be difficult.

In some instances, unexpected outcomes are due to unknown clinical issues. In other instances, unexpected outcomes can also be due to external factors causing a phenomenon with the instrumentation (either environmental or biological) of which indicators for these external factors would not exist in collected telemetry or results data. It can often be an arduous and expensive project to determine a cause of such problems in a research lab.

An additional difficulty of outlier analysis occurs when attempting to develop supporting logic for conditions that occur with low frequency. For example, low frequency conditions can come from interfering compounds or from diseases that are rare, but identification of such conditions are important for a successful diagnosis. Many approaches look to simply flag results as suspect when these conditions occur, which requires follow-up investigation.

SUMMARY

In an example, a computer-implemented method for providing diagnosis assistance is described. The method comprises receiving, at a server and from a remote computing device, initial data associated with a diagnostic test result of a subject and the initial data comprising one or more undetermined outliers, and selecting, by the server and from among a plurality of machine-learning logic, a machine-learning logic for execution based on a type of the diagnostic test result. The method also comprises determining, by the server executing the machine-learning logic and based on the initial data, a similarity between the initial data and diagnostic test result data stored in a database. The machine-learning logic is trained using diagnostic training data including test results and imaging labeled as known outliers. The method also comprises based on the similarity between the initial data and the diagnostic test result data being within a similarity threshold, providing an inquiry for display at the remote computing device to solicit additional information useful to resolve the one or more undetermined outliers, receiving input data from the remote computing device in response to the inquiry, and storing the input data in the database.

In another example, a server is described comprising one or more processors and non-transitory computer readable medium having stored therein instructions that when executed by the one or more processors, causes the server to perform functions. The functions comprise receiving, from a remote computing device, initial data associated with a diagnostic test result of a subject and the initial data comprising one or more undetermined outliers, and selecting, from among a plurality of machine-learning logic, a machine-learning logic for execution based on a type of the diagnostic test result. The functions also comprise determining, by executing the machine-learning logic and based on the initial data, a similarity between the initial data and diagnostic test result data stored in a database. The machine-learning logic is trained using diagnostic training data including test results and imaging labeled as known outliers. The functions also comprise based on the similarity between the initial data and the diagnostic test result data being within a similarity threshold, providing an inquiry for display at the remote computing device to solicit additional information useful to resolve the one or more undetermined outliers, receiving input data from the remote computing device in response to the inquiry, and storing the input data in the database.

In another example, a non-transitory computer readable medium is described having stored thereon instructions, that when executed by one or more processors of a computing device, cause the computing device to perform functions. The functions comprise receiving, from a remote computing device, initial data associated with a diagnostic test result of a subject and the initial data comprising one or more undetermined outliers, and selecting, from among a plurality of machine-learning logic, a machine-learning logic for execution based on a type of the diagnostic test result. The functions also comprise determining, by executing the machine-learning logic and based on the initial data, a similarity between the initial data and diagnostic test result data stored in a database. The machine-learning logic is trained using diagnostic training data including test results and imaging labeled as known outliers. The functions also comprise based on the similarity between the initial data and the diagnostic test result data being within a similarity threshold, providing an inquiry for display at the remote computing device to solicit additional information useful to resolve the one or more undetermined outliers, receiving input data from the remote computing device in response to the inquiry, and storing the input data in the database.

The features, functions, and advantages that have been discussed can be achieved independently in various examples or may be combined in yet other examples. Further details of the examples can be seen with reference to the following description and drawings.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

FIG. 7 shows a flowchart of an example of a method 200 for providing diagnostic assistance using the system of FIG. 1, according to an example implementation.

DETAILED DESCRIPTION

Figure 1:
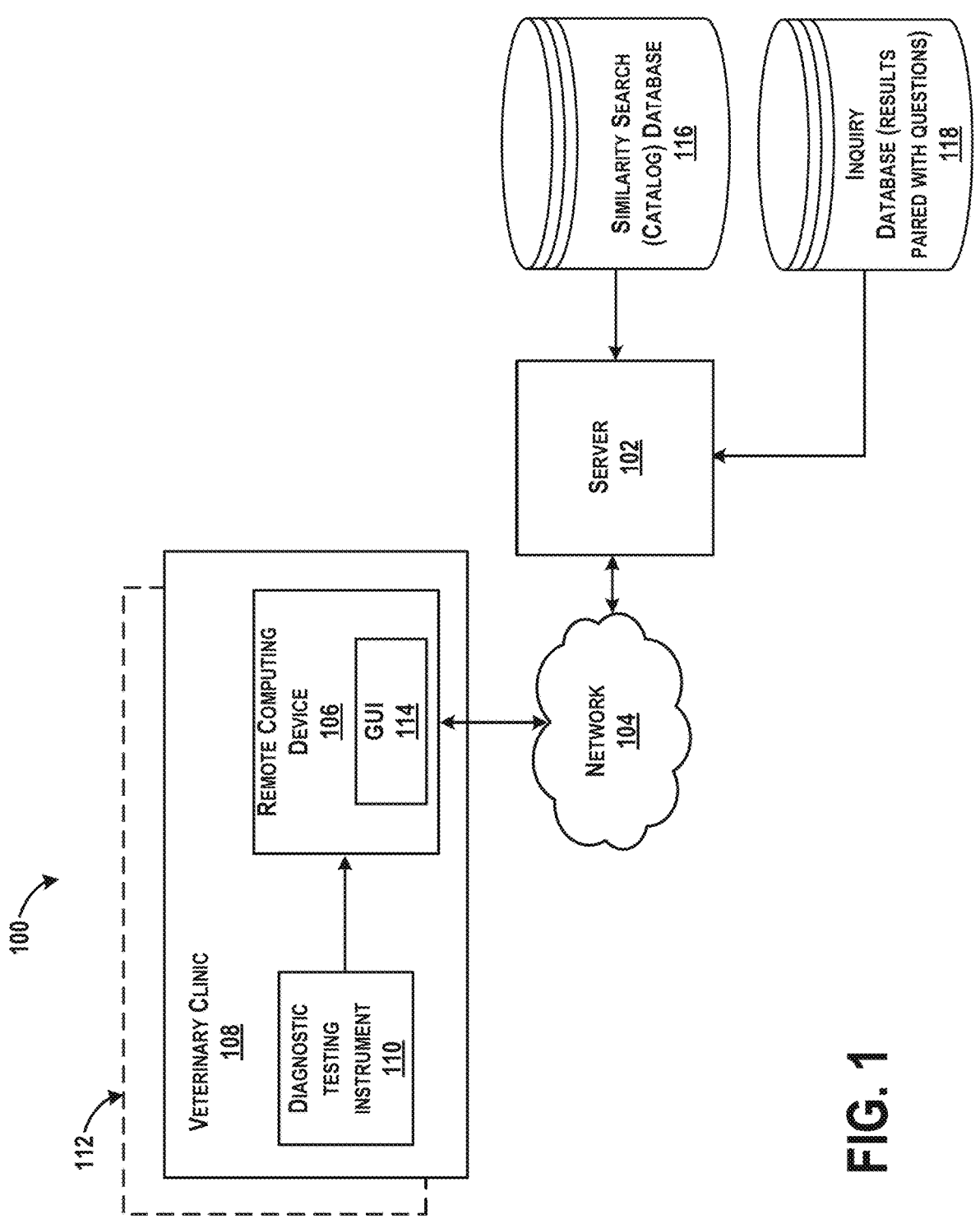
FIG. 1 illustrates an example of a system, according to an example implementation.

Disclosed examples will now be described more fully hereinafter with reference to the accompanying drawings. Indeed, several different examples may be described and should not be construed as limited to the examples set forth herein. Rather, these examples are described so that this disclosure will be thorough and complete and will fully convey the scope of the disclosure to those skilled in the art.

An example workflow of a scientist, engineer, or other researcher in research and development when evaluating opportunities to improve diagnostics, instruments, and other products is manual and arduous. The researcher manually reviews diagnostic results from instrumentation in a massive database looking for potential issues, and generally finds results that contained errors. For such erroneous results, additional data about the run on the instrument (e.g., sensor data, user inputs, calibration state) is reviewed to find a cause of the issue. To fully solve a problem, the scientist/engineer requires a meaningful distribution of situations in which a same anomaly occurs so that a solution may be robust and impactful. This process requires manual review and repeated erroneous results to be received, which adds considerable amounts of time to the feedback loop of the improvement process. For a case of diagnostics innovation, it is common to start an extensive sample collection effort so that gold standard approaches can be paired with field-collected data. This type of assessment can take years depending on sample frequency and development time.

Once a problem is identified and relevant data collected, the cause may not be clear. Causes of the issue can be related to a particular geographic region have shifting metrics due water or food supply, an unexpected illness, or even a misplaced cordless phone or radio affecting instrumentation operation. Determination of which, if any, of these causes requires a large amount of time for generation of hypotheses, design of experiments, and data collection. Recreating a problem in isolation so that a root cause is identifiable can take years and may never be completed.

Within examples described herein, technical solutions are provided to assist with outlier analysis and correction.

Output results of diagnostic instrumentation are analyzed, and when an outlier is identified, queries are generated and provided to a point of care provider to solicit information useful to resolve outliers with an undetermined cause. To generate the queries, the output results are compared to a population of samples (e.g., with known rare conditions) in a similarity search. The comparison is performed by executing machine learning logic to determine a similarity between the output results and diagnostic test result data stored in a database previously identified as a known outlier and a corresponding possibility for the outlier. The database further includes associated information tagged per each operation of any individual instrument that generated the output result. Thus, the queries are generated in substantially real-time or during a point of care treatment so that the point of care provider may collect additional data about the patient, environment, or testing instrumentation to resolve the undetermined outlier.

Systems are described including product research scientist tools (such as an interface for exploration and definition of specific data for customer questioning), product data science tools (such as algorithms for determining similarity on a myriad of data formats), product research and data science database (such as a catalog for storing interesting targets, similarity thresholds, similarity algorithm needed for that data, and questions to be prompted to the end user), and a customer facing interface (additions to customer facing applications facilitating the similarity database search, question prompting, and storage of the answers).

Methods and systems described herein facilitate rapid iterative improvements on projects by collecting supplemental information required to narrow root causes of anomalous or rare condition data. The root causes may not manifest in normally collected logging and diagnostic information within a fielded system, but could be identifiable with limited runs of targeted questioning. One example benefit of the system is that the system provides a direct line of communication between scientists and engineers working to improve products and customers using the products. Additionally, as prototype algorithms are developed, the algorithms are included with the similarity tool to identify additional cases as well as to provide real-time validation of the logic.

Thus, systems and methods described herein consider that some diagnostic test results may be inconclusive. As such, implementations of the disclosure are provided for matching current inconclusive test results with known inconclusive test results to then determine associated questions to present to the user, which when answered, enable a higher probability of resolving undetermined outliers.

Implementations of this disclosure thus provide technological improvements that are particular to computer technology, for example, those concerning similarity matching of undetermined outliers. Computer-specific technological problems, such as executing machine-learning logic in beneficial ways, can be wholly or partially solved by implementations of this disclosure. For example, implementation of this disclosure allows for current diagnostic test results to be matched to labeled diagnostic test results using a machine-learning logic to better understand the current results in view of prior similar inconclusive results.

The systems and methods of the present disclosure further address problems particular to computer devices and operation of diagnostic instruments, for example, those concerning analysis of diagnostic data. Utilizing machine-learning algorithms, trained on manually labeled diagnostic data, enables a more immediate and normalized analysis of the data. Thus, analysis of the diagnostic data can occur in a manner that is efficient and takes into account all patients' needs. Implementations of this disclosure can thus introduce new and efficient improvements in the ways in which data output from diagnostic instruments is analyzed to determine whether an inconclusive result is due to erroneous operation of the instrument or due to a rare unknown health condition of the subject.

Referring now to the figures, FIG. 1 illustrates an example of a system 100, according to an example implementation. The system 100 includes a server 102 accessible through a network 104 by multiple different computer systems. One set of the computer systems includes a remote computing device 106 residing at a veterinary clinic 108. In embodiments, a diagnostic testing instrument 110 is coupled to the remote computing device, the diagnostic testing instrument 110 operable to perform diagnostic testing of veterinary patients, for example. The diagnostic testing instrument 110 outputs diagnostic test results to the remote computing device 106 for analysis. While one veterinary clinic 108 is depicted in FIG. 1, it should be understood that this is merely an example, and systems according to the present disclosure can include any suitable number of veterinary clinics and associated computer systems, such as a second veterinary clinic 112 that includes the same or similar components as the veterinary clinic 108. As referred to herein, the term "veterinary clinics" includes any entity at which non-human animals receive medical care, and can include brick and mortar locations, mobile clinics, on-line virtual clinics, pop-up clinics, and the like.

In addition, while the example depicted in FIG. 1 includes one diagnostic testing instrument 110, it should be understood that this is merely an example, and embodiments according to the present disclosure can include any suitable number of diagnostic testing instruments associated with the veterinary clinic 108. Examples of the diagnostic testing instrument 110 include any one or combination of veterinary analyzers operable to conduct a diagnostic test of a sample of a patient (e.g., operable to determine hemoglobin amounts in a blood sample, operable to analyze a urine sample, and/or the like). Such veterinary analyzers include, for example and without limitation, a clinical chemistry analyzer, a hematology analyzer, a microscopic analyzer, a urine analyzer, an immunoassay reader, a sediment analyzer, a blood analyzer, a digital radiology machine, and/or the like. In one example, the remote computing device 106 is in communication with a veterinary analyzer of the diagnostic testing instrument 110 and is operable to receive diagnostic information from veterinary analyzer. The diagnostic testing instrument 110 outputs signals, such as signals indicative of diagnostic test results or other information, to the remote computing device 106.

In the system 100, the network 104 (e.g., Internet) provides access to the server 102 for all network-connected components. In some examples, more components of the system 100 may be in communication with the network 104 to access the server 102. Communication with the server 102 and/or with the network 104 may be wired or wireless communication (e.g., some components may be in wired Ethernet communication and others may use Wi-Fi communication). In still further examples, the network 104 provides access for the server 102 to communicate with the remote computing device 106 directly as well.

The system 100 enables a method for providing diagnosis assistance in instances in which diagnostic test results from the diagnostic testing instrument 110 include one or more undetermined outlier, for example. The term "undetermined outlier" as used herein refers to unexpected data falling outside of a configurable threshold, as described in greater detail herein. The presence of undetermined outliers in data from the diagnostic testing instrument 110 can be determined by the diagnostic testing instrument 110, the remote computing device 106, the server 102, or any suitable computing device communicatively coupled to the diagnostic testing instrument. The server 102 receives initial data associated with a diagnostic test result of a subject from the remote computing device 106 over the network 104. Within examples, the subject is a non-human patient, and the initial data includes flow cytometry data from an analyzer machine, urinalysis test result data, hematological data, or data related to other body fluids, fine needle aspirates, and/or lavages. More generally, the initial data includes outputs from any and all diagnostic testing instruments used to analyze samples collected from the subject. In some examples, the initial data further includes data associated with the subject such as a species, a breed, an age, a gender, and a weight, medical notes associated with a physical examination, a medical history record of the subject, and other information gained from the subject or pet owner at the time of examination.

The remote computing device 106 includes a graphical user interface (GUI) 114 for display, which is operable to receive input data to send to the server (e.g., data associated with the subject such as breed, age, etc., noted above). The GUI 114 is thus operable to receive inputs from the remote computing device 106, and to provide an updated display including inquiries received from the server 102.

In operation, the server 102 receives the initial data from the remote computing device 106, and the initial data including the diagnostic test result of the subject includes one or more undetermined outliers. The server 102 processes the data to determine prior similar test results and possible routes to take to arrive at a potential explanation for the one or more undetermined outliers. To do so, the server 102 selects from among a plurality of machine-learning logic, a machine-learning logic for execution based on a type of the diagnostic test result and then executes the selected machine-learning logic to determine a similarity between the initial data and diagnostic test result data stored in a database 116. Based on the similarity between the initial data and the diagnostic test result data being within a similarity threshold, the server 102 provides an inquiry for display at the remote computing device 106 (e.g., on the GUI 114) to solicit additional information useful to resolve the undetermined outlier. Accordingly, a veterinarian can obtain additional data to answer the inquiry at a time of point of care with the subject and input the additional data into the remote computing device 106. Subsequently, the server 102 will receive the input data from the remote computing device 106 in response to the inquiry, and store the input data in the database 116. In some examples, the answers to the inquiries include enough salient information for the server 102 to resolve the undetermined outlier, and the server 102 returns to the remote computing device 106 an accurate diagnosis of the diagnostic test result.

The system 100 includes an inquiry database 118 to which the server 102 is in communication for retrieving a corresponding inquiry, on the basis of the similarity match, to send to the remote computing device 106. In one example, the inquiry database 118 includes inquiries categorized per a type of diagnostic test result data and prioritized or ranked in a manner related to the similarity match. In one example, the inquiry database 118 includes inquiries that are paired with associated labels used to label diagnostic test result data in the similarity search database 116, such that once a match to a labeled diagnostic test result data is found, the label is used to retrieve corresponding inquiries to send to the remote computing device 106.

As a specific example, the diagnostic test result data is an output from a hematology analyzer including a dot plot used to classify cells in predictable manners. Processing of the output by the remote computing device 106 results in undetermined outliers, possibly due to the diagnostic test result data including uncommon results (e.g., unexpected cell size distribution, unexpected cell complexity distribution, or the like). Thus, the remote computing device 106 is programmed, on the basis of generating the undetermined outlier, one or more outliers, to send the diagnostic test results (as well as any and all information about the subject that has been entered into the GUI 114) to the server 102 for analysis. The server 102 executes a selected machine learning logic (trained on the basis of outputs of a hematology analyzer) to analyze the diagnostic test result data using the similarity search database 116. The server 102 is thus programmed with situations resulting in unknown/undetermined outliers, and pairs the situations with inquiries for further data collection. As a result, when the diagnostic test result data matches (to a sufficient similarity threshold) pre-programmed situations, the server 102 retrieves paired questions for the situations and sends the questions to the remote computing device 106 as an inquiry. In this example, the analysis of the diagnostic test result data is an unknown, but empirical studies in the past indicate a number of possible outcomes and more information is needed to rule out certain outcomes. The inquiries are provided to the remote computing device 106 to cause the veterinarian to prompt the pet owner with questions at a point of diagnostic care (e.g., when the subject is still at the veterinary clinic 108) so that necessary information can be obtained enabling a higher probability of determining an origin of the undetermined outlier or outliers.

As another specific example, the diagnostic test result data is an output from a urinalysis system. Processing of the output by the remote computing device 106 results in an undetermined outlier, possibly due to the diagnostic test result data including uncommon results (e.g., unidentified objects/sediment in the urine or the like). Thus, the remote computing device 106 is programmed, on the basis of generating the undetermined outlier, to send the diagnostic test results (as well as any and all information about the subject that has been entered into the GUI 114) to the server 102 for analysis. The server 102 executes a selected machine learning logic (trained on the basis of outputs of a urinalysis system) to analyze the diagnostic test result data using the similarity search database 116. The server 102 is thus programmed with situations resulting in unknown/undetermined outliers, and pairs the situations with inquiries for further data collection. As a result, when the diagnostic test result data matches (to a sufficient similarity threshold) pre-programmed situations, the server 102 retrieves paired questions for the situations and sends the questions to the remote computing device 106 as an inquiry. For a urinalysis sample collection, there are many ways of collecting the sample, and how the sample is collected can cause a different diagnostic test result (e.g., a free catch sample collection technique may result in some bacteria contamination or a sample collection from a catheter can result in contamination from other bacteria). Thus, the inquiries provided to the remote computing device 106 will prompt answers to enable resolution of an undetermined outlier.

Depending on the response to the inquiry, a diagnosis for consideration of a urinary tract infection (UTI) can be ruled out, for example.

As yet another example, the diagnostic test result data is output from an imaging system. For example and without limitation, imaging systems can include computed tomography (CT) systems, digital microscopy systems, x-ray systems and the like. Processing of the output by the remote computing device 106 results in an undetermined outlier, possibly due to the diagnostic test result data including uncommon results. In examples in which the imaging system is a digital microscopy system, uncommon results may be unidentified objects in a sample (e.g., in instances in which the sample is an ear swab), uncommon morphology or unidentified cell types (e.g., in instances in which the sample is blood or a fine needle aspirate), and the like. Thus, the remote computing device 106 is programmed, on the basis of generating the undetermined outlier, to send the diagnostic test results (as well as any and all information about the subject that has been entered into the GUI 114) to the server 102 for analysis. The server 102 executes a selected machine learning logic (trained on the basis of outputs of an imaging system) to analyze the diagnostic test result data using the similarity search database 116. The server 102 is thus programmed with situations resulting in unknown/undetermined outliers, and pairs the situations with inquiries for further data collection. As a result, when the diagnostic test result data matches (to a sufficient similarity threshold) pre-programmed situations, the server 102 retrieves paired questions for the situations and sends the questions to the remote computing device 106 as an inquiry. In this example, the analysis of the diagnostic test result data is an unknown, but empirical studies in the past indicate a number of possible outcomes and more information is needed to rule out certain outcomes. The inquiries are provided to the remote computing device 106 to cause the veterinarian to prompt the pet owner with questions at a point of diagnostic care (e.g., when the subject is still at the veterinary clinic 108) so that necessary information can be obtained enabling a higher probability of determining an origin of the undetermined outlier or outliers.

Example inquiries for diagnostic test result data output from an imaging system are selected on a basis of the pre-programmed situations. For example, when bacteria is identified in a gray zone region where there is some identified bacteria but not enough to trigger a threshold amount programmed to report bacteria, then the inquiries provided include prompting the veterinarian to ask questions of the pet owner to understand if there are clinical signs of a bacteria infection that could cause the threshold amount to be lowered or adjusted for this patient for subsequent diagnosis. In another example, if parasitic organisms are potentially identified in the sample images (e.g., including bacteria, fungus, worms or heartworm, and others), then the inquiries provided including prompting for confirmation tests for those parasites to be performed including enzyme-linked immunoassay (ELISA) tests (e.g., Heartworm test), polymerase chain reaction (PCR) tests, or other serology. In another example, if conditions of malignancy are present in the sample images, then the inquiries provided include prompting for additional testing to include histology, immunohistochemistry, immunocytochemistry, or other.

The questions presented in the inquiry can be directed to conditions of the subject, such as physical conditions observable by the veterinarian. The questions presented in the inquiry can further be directed to conditions of the testing environment, such as relates to the sample or operation of the diagnostic testing instrument. There may be any number of issues causing the undetermined outlier, and with the server 102 analyzing the diagnostic test results in view of a large scale of prior diagnostic test result data in the database 116, the server 102 finds a match (within a similarity threshold) and a prior outcome can be determined upon responding to the inquiry in many situations.

Figure 2:
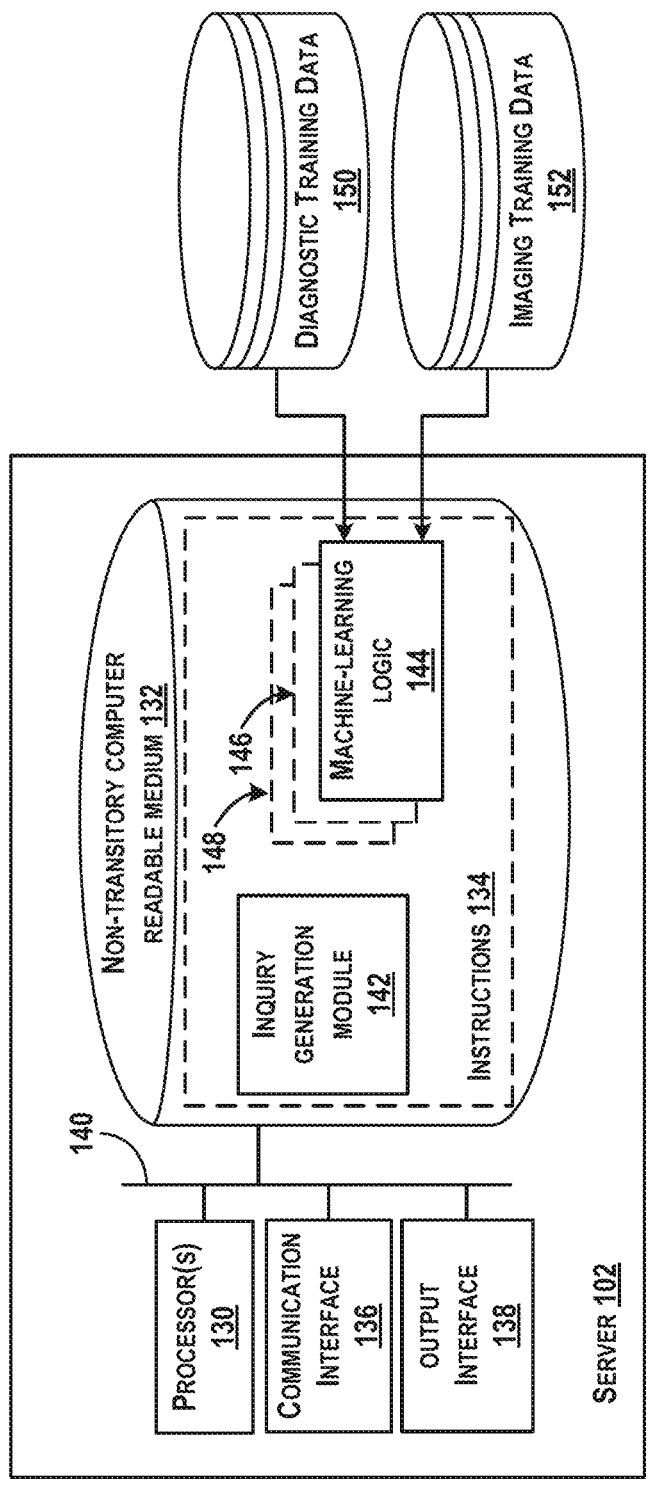
FIG. 2 illustrates an example of a server of the system of FIG. 1, according to an example implementation.

FIG. 2 illustrates an example of the server 102 in FIG. 1, according to an example implementation. Within examples herein, functions described for processing diagnostic test result data are performed by the remote computing device 106, by the server 102, or by a combination of the remote computing device 106 and the server 102. Thus, although FIG. 2 illustrates the server 102, the components of the remote computing device 106 are the same as the components of the server 102 within some examples, depending on where a function is programmed to be performed in a specific implementation.

The server 102 includes one or more processor(s) 130, and non-transitory computer readable medium 132 having stored therein instructions 134 that when executed by the one or more processor(s) 130, causes the server 102 to perform functions for processing diagnostic test result data, as well as management and control of diagnostic instruments and for generation of inquiries for display on a GUI, for example.

To perform these functions, the server 102 also includes a communication interface 136, an output interface 138, and each component of the server 102 is connected to a communication bus 140. The server 102 may also include hardware to enable communication within the server 102 and between the server 102 and other devices (not shown). The hardware may include transmitters, receivers, and antennas, for example. The server 102 may further include a display (not shown).

The communication interface 136 may be a wireless interface and/or one or more wireline interfaces that allow for both short-range communication and long-range communication to one or more networks or to one or more remote devices. Such wireless interfaces may provide for communication under one or more wireless communication protocols, Bluetooth, WiFi (e.g., an institute of electrical and electronic engineers (IEEE) 802.11 protocol), Long-Term Evolution (LTE), cellular communications, near-field communication (NFC), and/or other wireless communication protocols. Such wireline interfaces may include an Ethernet interface, a Universal Serial Bus (USB) interface, or similar interface to communicate via a wire, a twisted pair of wires, a coaxial cable, an optical link, a fiber-optic link, or other physical connection to a wireline network. Thus, the communication interface 136 may be configured to receive input data from one or more devices, and may also be configured to send output data to other devices.

The non-transitory computer readable medium 132 includes or takes the form of memory, such as one or more computer-readable storage media that can be read or accessed by the one or more processor(s) 130. The non-transitory computer readable medium 132 can include volatile and/or non-volatile storage components, such as optical, magnetic, organic or other memory or disc storage, which can be integrated in whole or in part with the one or more processor(s) 130. In some examples, the non-transitory computer readable medium 132 is implemented using a single physical device (e.g., one optical, magnetic, organic or other memory or disc storage unit), while in other examples, the non-transitory computer readable medium 132 is implemented using two or more physical devices. The non-transitory computer readable medium 132 thus is a computer readable storage, and the instructions 134 are stored thereon. The instructions 134 include computer executable code.

The one or more processor(s) 130 may be general-purpose processors or special purpose processors (e.g., digital signal processors, application specific integrated circuits, etc.). The one or more processor(s) 130 receive inputs from the communication interface 136 (e.g., x-ray images), and process the inputs to generate outputs that are stored in the non-transitory computer readable medium 132. The one or more processor(s) 130 are configured to execute the instructions 134 (e.g., computer-readable program instructions) that are stored in the non-transitory computer readable medium 132 and are executable to provide the functionality of the server 102 described herein.

The output interface 138 outputs information for transmission, reporting, or storage, and thus, the output interface 138 may be similar to the communication interface 136 and can be a wireless interface (e.g., transmitter) or a wired interface as well.

Within examples, the instructions 134 include specific software for performing the functions including an inquiry generation module 142, and a plurality of machine-learning logic including machine-learning logic 144, 146, and 148.

With respect to the inquiry generation module 142, the server 102 has access to or is in communication with the inquiry database 118 that stores questions mapping to identified undetermined outliers that map to stored and identified outliers in the similarity search database 116. Thus, when a match is found between received diagnostic test result data that is within a similarity threshold to diagnostic test result data in the similarity search database 116, corresponding questions from the inquiry database 118 are retrieved by the server 102 and sent to the remote computing device 106.

The plurality of the machine-learning logic 144, 146, and 148 are each selectable for execution based on a type of a received diagnostic test result at the server 102. Each initial data received at the server 102 from the remote computing device 106 includes an identifier, for example, of a type of diagnostic testing instrument that output the data. The server 102 selects one of the machine-learning logic 144, 146, and 148 for execution based on the type of diagnostic data and/or type of diagnostic testing instrument that output the data.

Although three different machine-learning logic 144, 146, and 148 are shown, the server 102 and the instructions 134 may include more or fewer machine-learning logic for different testing instrumentation.

Each of the machine-learning logic 144, 146, and 148 are trained using instrumentation output data labeled as an outlier, and such training data is accessible in associated databases. As shown in FIG. 2, one of the machine-learning logic 144, 146, and 148 is trained using diagnostic training data 150 labeled as an outlier, and another (or the same) machine-learning logic is trained using imaging training data 152 labeled as an outlier.

In one example operation, the server 102 receives from the remote computing device 106 initial data associated with a diagnostic test result of a subject including one or more undetermined outliers, and then the server 102 selects from among the plurality of the machine-learning logic 144, 146, and 148, a machine-learning logic for execution based on a type of the diagnostic test result. By the server 102 executing the selected machine-learning logic and based on the initial data, a similarity between the initial data and diagnostic test result data stored in the database 116 is determined. When the similarity is within a similarity threshold, the server 102 uses the similarity retrieve an associated inquiry (which may include one question or a set of questions) from the inquiry database 118, and provides the inquiry for display at the remote computing device 106 to solicit additional information useful to resolve the undetermined outlier. Following, the server 102 receives input data from the remote computing device 106 in response to the inquiry, and stores the input data in the database 116.

Execution of the machine-learning logic 144, 146, and 148 to perform analysis of the diagnostic test results removes any human bias and generates normalized results for all inputs.

Referring to the machine-learning logic 144, 146, and 148, many types of functionality and neural networks can be employed to perform functions of specific machine-learning algorithms to carry out functionality described herein. In one example, the machine-learning logic 144, 146, and 148 use statistical models to generate outputs without using explicit instructions, but instead, by relying on patterns and inferences by processing associated training data.

The machine-learning logic 144, 146, and 148 can thus operate according to machine-learning tasks as classified into several categories. In supervised learning, the machine-learning logic 144, 146, and 148 build a mathematical model from a set of data that contains both the inputs and the desired outputs. The set of data is sample data known as the "training data", in order to make predictions or decisions without being explicitly programmed to perform the task. For example, the machine-learning logic 144, 146, and 148 utilizes the diagnostic training data 150 and the image training data 152 within comparisons to identify matches of received diagnostic test result data to the labeled diagnostic test result data that are within a similarity threshold. When such a match is found, the labeled diagnostic test result data is reference as a label to be applied to the received diagnostic data and the label is further used as a reference to retrieve an appropriate inquiry from the inquiry database 118. Thus, the labels are paired with both prior analyzed diagnostic test result data and inquiries to form inquiry/label pairs, for example.

In another category referred to as semi-supervised learning, the machine-learning logic 144, 146, and 148 develop mathematical models from incomplete training data, where a portion of the sample input does not have labels. A classification algorithm can then be used when the outputs are restricted to a limited set of values.

In another category referred to as unsupervised learning, the machine-learning logic 144, 146, and 148 builds a mathematical model from a set of data that contains only inputs and no desired output labels. Unsupervised learning algorithms are used to find structure in related training data, such as grouping or clustering of data points. Unsupervised learning can discover patterns in data, and can group the inputs into categories.

Alternative machine-learning algorithms may be used to learn and classify types of diagnostic test results to consider for generating the inquiries, such as deep learning though neural networks or generative models. Deep machine-learning may use neural networks to analyze prior test results through a collection of interconnected processing nodes. The connections between the nodes may be dynamically weighted. Neural networks learn relationships through repeated exposure to data and adjustment of internal weights. Neural networks may capture nonlinearity and interactions among independent variables without pre specification. Whereas traditional regression analysis requires that nonlinearities and interactions be detected and specified manually, neural networks perform the tasks automatically.

Still other machine-learning algorithms or functions can be implemented to determine a similarity match and generate the inquiries, such as any number of classifiers that receives input parameters and outputs a classification (e.g., attributes of the image). Support vector machine, Bayesian network, a probabilistic boosting tree, neural network, sparse auto-encoding classifier, convolutional neural network (e.g., for image-based classifiers) or other known or later developed machine-learning algorithms may be used. Any semi-supervised, supervised, or unsupervised learning may be used. Hierarchal, cascade, or other approaches may be also used.

The machine-learning logic 144, 146, and 148 may thus be considered an application of rules in combination with learning from prior labeled data to identify appropriate outputs. Analyzing and relying on prior labeled data allows the machine-learning logic 144, 146, and 148 to apply patterns of diagnostic test results and associated inquiries that are generally issued when such test results are observed, for example.

Thus, the machine-learning logic 144, 146, and 148 take the form of one or a combination of any of the herein described machine-learning algorithms, for example.

Figure 3:
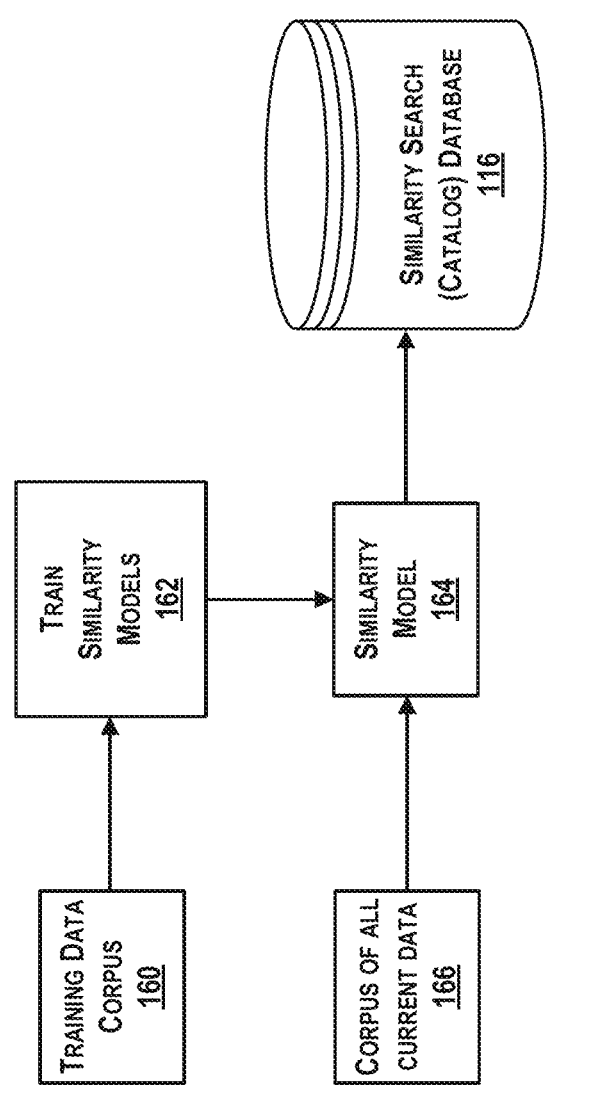
FIG. 3 is a block diagram illustrating an example workflow for creating and training a similarity search models used for the machine-learning logic of the system of FIG. 1, according to an example implementation.

FIG. 3 is a block diagram illustrating an example workflow for creating and training a similarity search models used for the machine-learning logic, according to an example implementation. Modern unsupervised machine learning techniques are available to learn feature embeddings and aspects of proprietary data. A machine learning logic model with access to tens of thousands (or more) data examples is executable to learn and apply data processing about a specific type of data. Such models are trained with rules, encoding domain knowledge that allows for how a scientist/engineer may want to search the data, and what level of granularity constitutes a similar threshold within a given context for a specific type of diagnostic test result data. This approach allows for accurate similarity search on numerous data samples for exploration and identification. Example machine-learning logic reduce data to a numeric vector that is responsive to distance metric determinations. This functionality allows for a scientist to ask for a "closest 500 data examples to one of interest" based on the converted distance metrics in order to find matches.

As shown in FIG. 3, training data corpus 160 that includes diagnostic test result data labeled as a known outlier generated by manual labeling via review by humans is used to train similarity models 162, such as the machine-learning logic 144, 146, and 148. Following, a trained similarity model 164 results that is executed to process a corpus of all current data 166 that includes newly received and unlabeled diagnostic test result data. Outputs of execution of the similarity model 164 include a similarity determination, such as a match to a labeled diagnostic test result data within a similarity threshold. The similarity model 164 also outputs, based on the similarity being found, the newly received data with an associated label to the similarity search database 116 to increase the amount of cataloged data.

Figure 4:
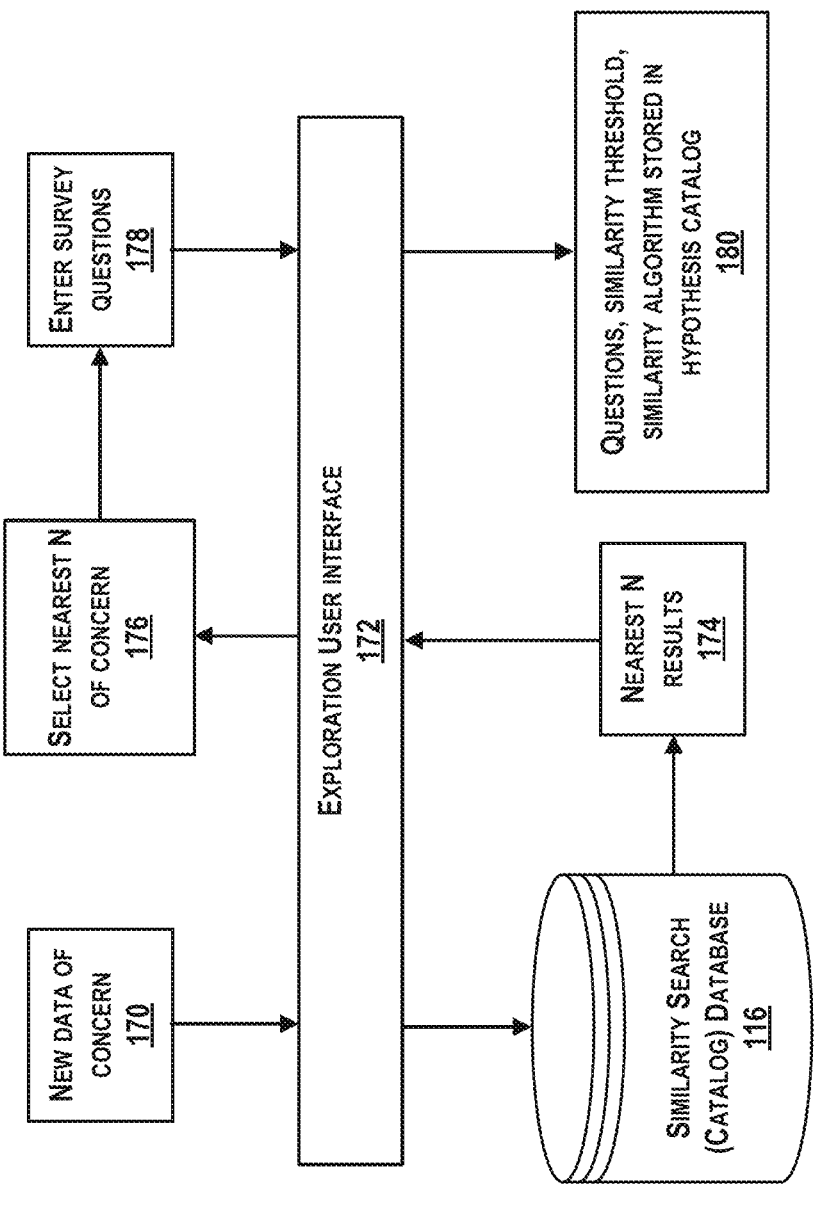
FIG. 4 is a block diagram illustrating an example workflow for interrogation of the similarity search model for the purposes of exploring available data and generating associated queries using the system of FIG. 1, according to an example implementation.

FIG. 4 is a block diagram illustrating an example workflow for interrogation of the similarity search model for the purposes of exploring available data and generating associated queries, according to an example implementation. New data of concern 170, such as newly generated diagnostic test result data, is uploaded to an exploration user interface 172 (e.g., the GUI 114 of the remote computing device 106), to be sent via the network 104 to the server 102. The server 102

(not shown) executes the similarity search models via access to the similarity search database 116 to output a nearest N results that match to the new data. Such results are provided by the server 102 to the remote computing device 106 for display on the GUI 114, and an amount of the nearest N results are selected as shown at 176 so that associated survey questions are entered as shown at 178. In addition to generating the questions for the inquiry, a similarity threshold for what constitutes a similar match is input.

The similarity threshold varies based on the corpus of data, scale of current throughput, and rarity of a case being analyzed. Because each example of data is represented by a vector, transformed by a neural network, standard distance metrics are utilized (vector_1-vector_2) or cosine distance, Manhattan distance, etc., depending on the corpus and needs of the effort in order to determine matches.

As an example, a scientist wants to test a hypothesis and so a diagnostic data of concern is selected and searched for a nearest 1000 out of a latest 100,000 data that has been received. The scientist finds a similarity they are concerned with degrades after the 600th closest example, and that example has a distance of an arbitrary number, for this example, let's say distance of eight. Any new run received that is a subtracted vector distance to the target less than eight is a candidate for question prompting. A custom threshold is subjective and tunable to both data at hand, vector size based on neural network capacity needs, statistical significance required for the hypothesis, not over prompting users, and distance of concern to the scientist. Alternate threshold metrics can be determined that look for a proportion of the data set instead of a fixed count, and the largest vector distance for that proportion of samples in the reference database provides the threshold for that query. Alternatively, the reference database can be compared with the reference data and a histogram of the vector distance can be generated and logic to remove the "normal" population (biggest section in the data set and not representing the data of interest) could be removed and "tail" statistics can be derived to determine the vector distance correlating to the cutoff threshold. Additional similar approaches can be employed. Further, this process can be iterative where the first threshold allows a wider range of results to ensure that the condition of interest (high sensitivity) is captured and the threshold and training data can be refined as more data comes in to improve specificity by rejecting vector distances that are not related to the condition of interest.

The metrics, questions, and data of concern are then submitted to the similarity search database 116 in a feedback manner, as shown at block 180.

Figure 5:
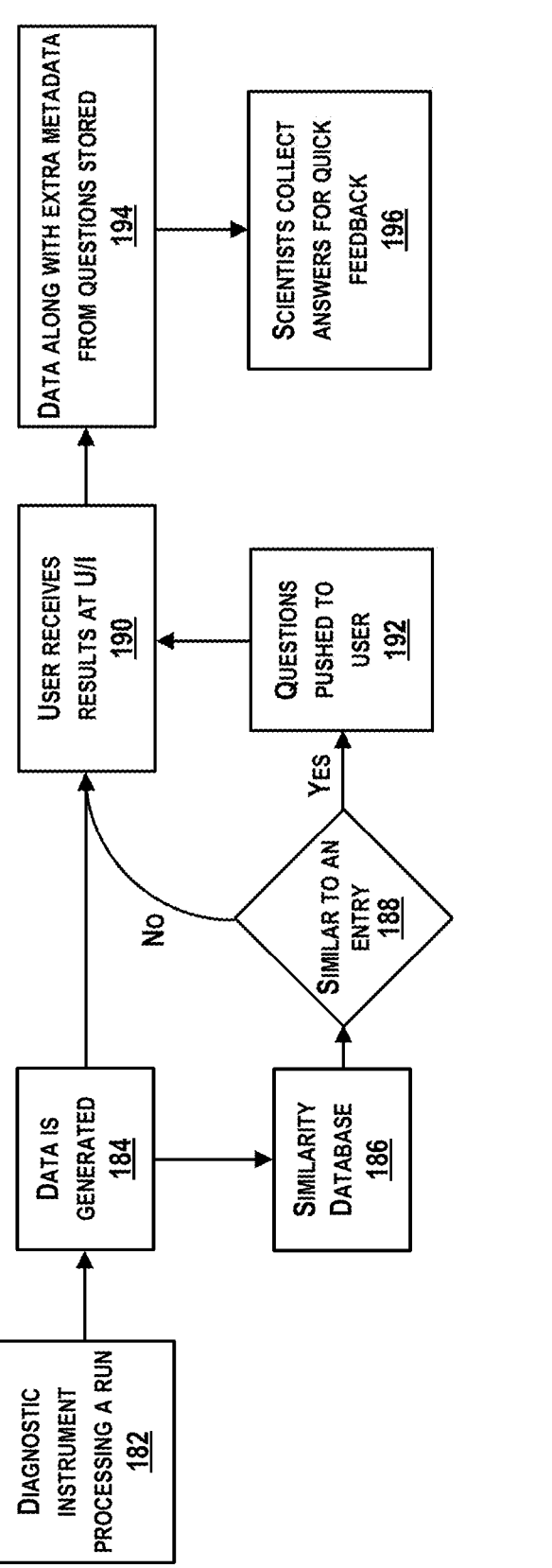
FIG. 5 is a block diagram illustrating an example workflow for providing diagnosis assistance using the system of FIG. 1, according to an example implementation.

FIG. 5 is a block diagram illustrating an example workflow for providing diagnosis assistance, according to an example implementation. For a user to be prompted while a subject or patient is fresh in memory, detecting similarity needs to occur quickly. The diagnostic instrumentation or remote computing device 106 running the instrument or communicating with the instrument in real time will need to check the similarity search database (also referred to as a hypothesis catalog) for similar entries. Alternatively, the outputs of the instrumentation are provided to a server for checking the similarity database. Thus, in FIG. 5, a diagnostic instrument processing a run at block 182 and diagnostic test result data is generated at block 184. The data at block 184 is provided to the remote computing device 106 or the server 102 to check the similarity database at block 186. The data is also provided to a user of the remote computing device 106 at the GUI 114, as shown at block 190.

Note that in some examples, similarity logic is implemented on the local diagnostic instrument or the remote computing device 106 that is analyzing the sample, which then interacts with the server 102 for information such as a similarity vector and threshold to determine results to return if the threshold is met. In this example, the inquires are then received from the server 102 at the remote computing device 106. Functionality may be performed more quickly and the implementation may depend on how large the data files are as a basis for performing processing locally or on the server 102.

In some examples, the similarity database contains the following for each entry: data of interest (e.g., labeled diagnostic test results), a similarity algorithm to use (e.g., an identifier for which of the machine-learning logic 144, 146, and 148 to use), similarity thresholds or metrics required for qualifying matches as "similar", and corresponding questions to prompt the user/customer. A given diagnostic run would then be compared with the similarity database to see if any of the data are similar and if so, prompt the user with the questions.

In an example, the initial data associated with the diagnostic test result of a subject includes one or more of a species, an age, and a weight, of the subject as well as a test result from a hematology analyzer, and then determining the similarity between the initial data and the diagnostic test result data stored in the similarity database includes matching the initial data and the diagnostic test result data stored in the similarity database from subjects of a same species and having age and weight within a preset range.

Upon matching to data in the similarity database as shown at block 188, questions are pushed to the user through the GUI 114 at the remote computing device 106 as shown at blocks 190 and 192. As mentioned above, the similarity database stores inquiry and similarity threshold pairings so that the server or remote computing device selects from the database, the inquiry for display based on the similarity threshold.

Examples of questions pushed to the user vary on the type of diagnostic test result data being analyzed. In one instance, when data is received that includes imaging data of the subject (e.g., x-rays or ultrasound data), questions pushed to the user include requesting additional subject data about the subject including one or more of a breed, an age, and information related to any medication taken. In another instance, when data is received that includes flow cytometry data, questions pushed to the user include requesting that an aliquot of a sample of the subject be sent to a lab for testing. In another instance, when data is received that includes flow cytometry data from an analyzer machine, questions pushed to the user include requesting additional hardware data about the analyzer machine or about operating conditions of the analyzer machine to solicit additional information useful to determine whether any abnormality is due to operation of the analyzer machine or due to a morphology of the diagnostic test result. In another instance, when data is received that includes urinalysis test result data, questions pushed to the user include requesting information related to how a urine sample was collected.

After the questions are answered, the workflow needs to place metadata that identifies the individual run and the answers to the questions back into the similarity database for collection by scientists, as shown by blocks 194 and 196. The similarity database includes, in one example, a referential database and the metadata that identifies the initial data along with the input data is stored together in the database.

Figure 6:
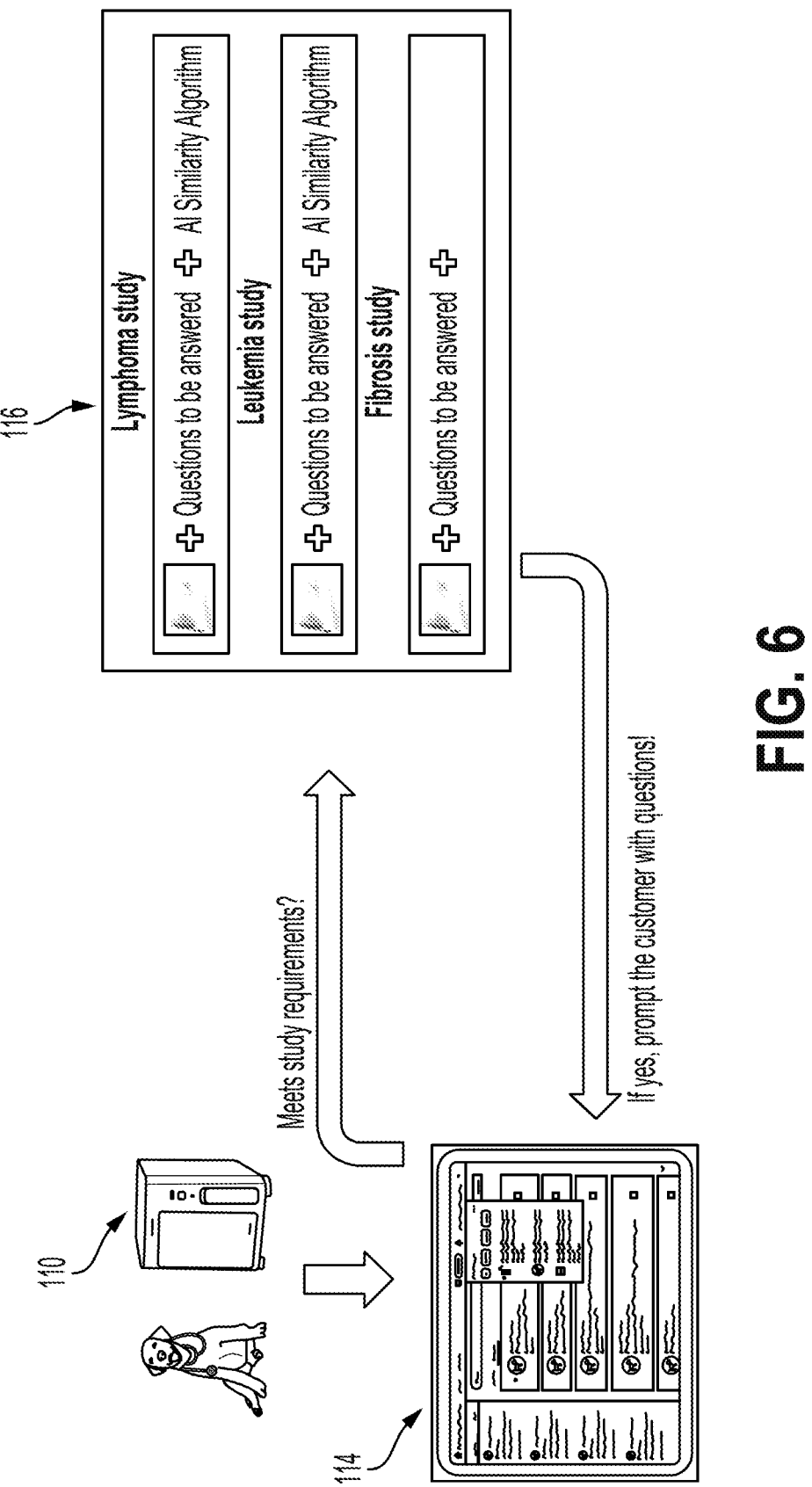
FIG. 6 is another example workflow for providing diagnosis assistance using the system of FIG. 1, according to an example implementation.

FIG. 6 is another example workflow for providing diagnosis assistance, according to an example implementation. FIG. 6 pictorially illustrates a subject (e.g., a dog) for which a biologic sample was taken and analyzed by a diagnostic testing instrument 110 and outputs including diagnostic test result data provided to the GUI 114 of the remote computing device 106. In some examples, the remote computing device 106 performs a pre-analysis of the diagnostic test results, and when an undetermined outlier results (i.e., unclear or insufficient data to come to a conclusion for what the diagnostic test results indicate), then the remote computing device 106 either sends the diagnostic test results to the server 102 for analysis or accesses the similarity database itself. Thus, in some instances, the remote computing device 106 determines firstly whether the diagnostic test results meet study requirements for processing by the similarity search.

Upon meeting the study requirements, associated similarity searches are run on the diagnostic test result data. As mentioned above, the similarity search database 116 contains a similarity algorithm to use (e.g., an identifier for which of the machine-learning logic 144, 146, and 148 to use) and corresponding questions to prompt the user/customer for each data entry and per type of data. As shown in FIG. 6, example types of data include data associated with a lymphoma study, a leukemia study, and a fibrosis study. Many other types of data are possible as well.

When matches are found, the associated questions are sent back to the remote computing device 106 to collect answers for analysis that are also saved with the corresponding diagnostic test result data.

Below are a few examples providing insight into practical uses of the systems and methods described herein.

A first example relates to flow cytometry data used for hematology and supporting new diagnostic functionality discovery and development. Hematology analyses can utilize several technologies for determining reported complete blood count output. Part of the output commonly includes graphical representations of cells to confirm algorithms and system functionality for the run. The graphical representations provide physical insight into a morphologic presentation of cells to the analyzer. A researcher might have a physical expectation that a particular presentation of cells on the graphical presentation be indicative of a disease state that has not previously been identified, such as malignant cells for example. After finding a case that provides a desired graphical presentation, the researcher can ask the similarity search system (e.g., the system 100 in FIG. 1) to find a population of runs from the field that are most closely matched to that presentation. Once the researcher confirms that the condition happens at some rate and across a number of analyzers, questions can then be generated. Specifically, tools can watch runs as customers perform them and when the output of the run resembles reference stored data, questions presented can include asking the customer to send an aliquot of the sample to a research and development lab for confirmation testing using current high standard techniques such as dedicated antibody labels and other techniques like blood film reviews by clinical pathologists. Once enough samples have been received and confirmed, an algorithm can be developed to trigger a presence of the disease state when the specific signature is presented. The system can then implement the new algorithm logic on every run performed in the field and provide statistics and explicit examples where the logic triggers as positive, while continuing to ask the customer to send the sample for analysis.

The algorithm can then be tuned for sensitivity and specificity and retested with the same tools.

Thus, when a set of hematological data examples are determined as being closest matches to the initial data, where a number of examples within the set of hematological data examples has a preset maximum (e.g., a statistically relevant amount), matches are found and a plurality of inquiries are selected for display mapping to the set of hematological data examples.

A second example relates to imaging data used for morphology analysis and supports expanded detection capabilities. Digital imaging techniques provide images that correlate to microscopy images used in medicine for diagnostics. Algorithms can be applied to those images to perform the analyses that are otherwise performed by highly trained medical personnel, such as clinical pathologists. The algorithms are based on samples that are identified during development. A common approach for system development is to develop automated algorithms based on the most found elements for release and then to add new functionality when enough data is collected of those specific low frequency but highly diagnostic elements. The similarity search system can be used to find like examples once a first is found. Like the hematology example above, the large breadth of examples in the database provides a large warehouse where low frequency events can be found rapidly. A following process is like the hematology process where the data coming back is used for development. It is possible to ask the customer for the samples, for glass slides of the samples, or for specific features about the sample donor, such as breed, age, medication, or other clinical signs.

A third example relates to a flow cytometry system used in hematology and identifies a condition where the presented data demonstrates a hardware failure in the system that the internal logic does not yet capture. If a flow cytometer has a rare event where fluidics enter an unstable state, presented graphical data can look abnormal. It is required for the system to identify when the abnormality is due to the analyzer operation or due to the morphology of the sample. The similarity search system can find examples where abnormal presentations of data occur and ask questions about a health state of the subject. If an animal is healthy, there are few reasons to expect abnormal data presentations and these examples can be used to provide logic to minimally flag the results or better yet identify what occurred during the run so it can be corrected and no longer impact the analyzer. Examples could be electromagnetic interference from a nearby router, centrifuge, or other source that only impacts the system when they are engaged. These are exceedingly difficult to reproduce in research and development and data from the customer can be uniquely helpful in identifying the driving factors.

FIG. 7 shows a flowchart of an example of a method 200 for providing diagnostic assistance, according to an example implementation. Method 200 shown in FIG. 7 presents an example of a method that could be used with the system 100 shown in FIG. 1, the server 102, shown in FIG. 1, or the remote computing device 106 shown in FIG. 1, for example. Further, devices or systems may be used or configured to perform logical functions presented in FIG. 7. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. Method 200 may include one or more operations, functions, or actions as illustrated by one or more of blocks 202-212. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present examples. In this regard, each block or portions of each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block or portions of each block in FIG. 7, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

At block 202, the method 200 includes receiving, at a server and from a remote computing device, initial data associated with a diagnostic test result of a subject and the initial data comprising one or more undetermined outliers. In some examples, block 202 includes displaying a dot plot of the initial data at the server, such as when the initial data relates to hematological data.

At block 204, the method 200 includes selecting, by the server and from among a plurality of machine-learning logic, a machine-learning logic for execution based on a type of the diagnostic test result.

At block 206, the method 200 includes determining, by the server executing the machine-learning logic and based on the initial data, a similarity between the initial data and diagnostic test result data stored in a database. The machine-learning logic is trained using diagnostic training data including test results and imaging labeled as known outliers.

In one example, the initial data associated with the diagnostic test result of a subject includes one or more of a species, an age, and a weight, of the subject as well as a test result from a hematology analyzer, and block 206 includes determining the similarity between the initial data and the diagnostic test result data stored in the database from subjects of a same species and having age and weight within a preset range.

At block 208, the method 200 includes based on the similarity between the initial data and the diagnostic test result data being within a similarity threshold, providing an inquiry for display at the remote computing device to solicit additional information useful to resolve the one or more undetermined outliers.

In one example, block 208 includes providing the inquiry for display in substantially real-time upon generation and transmission of the diagnostic test result of the subject to the server. In this context, real-time means within a time required for processors to analyze and execute machine-learning logic based on receiving diagnostic test result data. Generally, real-time is thus related to processing times of the processors as well as a transmission time of data across the network 104, for example.

Within examples, the method 200 additionally includes receiving imaging data of the subject, and block 208 includes providing the inquiry requesting additional subject data about the subject including one or more of a breed, an age, and information related to any medication taken. Further, in some examples, following block 208, the method 200 includes based on receiving a threshold number of additional subject data from a plurality of subjects and generating a confirmed diagnosis due to analysis of the threshold number of additional subject data, tuning the machine-learning logic and the similarity threshold. Examples of threshold number of additional subject data include one hundred more individual test results, one thousand more individual test results, or more as configured, resulting in a new corpus of labeled training data.

In another example, the method 200 additionally includes receiving flow cytometry data, and block 208 includes providing the inquiry requesting that an aliquot of a sample of the subject be sent to a lab for testing. Further, in some examples, following block 208, the method 200 includes based on receiving a threshold number of samples from a plurality of subjects and generating a confirmed diagnosis due to analysis of the threshold number of samples, tuning the machine-learning logic and the similarity threshold.

Thus, the method 200 is executable to tune the machine-learning logic based on updates to training data that include additions of more labeled diagnostic training data.

In still another example, the method 200 additionally includes receiving flow cytometry data from an analyzer machine, and block 208 includes providing the inquiry requesting additional hardware data about the analyzer machine or about operating conditions of the analyzer machine to solicit additional information useful to determine whether any abnormality is due to operation of the analyzer machine or due to a morphology of the diagnostic test result.

In still another example, the method 200 additionally includes receiving urinalysis test result data, and block 208 includes providing the inquiry requesting information related to how a urine sample was collected.

In still another example, block 206 includes determining a set of hematological data examples being closest matches to the initial data and a number of examples within the set of hematological data examples has a preset maximum, and block 208 includes selecting a plurality of inquiries for display mapping to the set of hematological data examples and the inquiry for display is one of the plurality of inquiries for display.

In yet another example, the database stores inquiry and similarity threshold pairings, and the method 200 additionally includes selecting from the database, the inquiry for display based on the similarity threshold.

At block 210, the method 200 includes receiving input data from the remote computing device in response to the inquiry.

At block 212, the method 200 includes storing the input data in the database. In one example, the database is a referential database, and block 212 includes storing metadata that identifies the initial data along with the input data to catalog and/or index results.

The method 200 is described for providing diagnostic assistance, which includes assistance with any type of understanding of the diagnostic test result data. Examples include diagnostic assistance with identifying an unknown biological or clinical issue with the subject, as well as assistance with identifying issues with the diagnostic instrumentation or testing environment (e.g., signal interference and other non-biological artifacts affecting test results). Generally, the diagnostic assistance provided by the systems and methods herein is possible for all types of diagnostic test result data cataloged in the similarity search database 116.

With the systems and methods described herein, access to a large dataset of labeled diagnostic data is leveraged to identify an amount and type of missing information needed in order to arrive at a more probable diagnosis and an improved workflow.

Many advantages and benefits are seen by implementing the systems and methods herein including increased speed to determine a root cause failure of machines in the field (e.g., when diagnostic test result data is indeterminate due to failure of the testing instrumentation), decreased time to identify low-frequency diagnosis conditions (e.g., such as rare biological conditions for which much data and analysis is needed to identify), rapid aggregation of data for new modeling (e.g., such as modeling more machine failure or incorrect operation issues), rapid algorithm development of new instruments, ease of data labeling when using data from an on-market instrument as truth for a new instrument, and identifying rare field cases in real-time.

The example system and methods described herein can also be run in iterations as well, such as to capture answers to questions and the answers may trigger further questions to present for consideration.

Generally, operation of the systems and methods herein enables analysis of diagnostic test data, for which currently results in an undetermined outlier, to move more closely to a known diagnosis on the basis of additional data being provided. The systems and methods herein are beneficially used in analysis of diagnostic test results of animals, as compared to test results of humans, due to the large amount of differences in test data due to different breeds, species, etc. and differences in types of food consumed, lifestyles, etc.

With reference to FIG. 2, and throughout the disclosure, some components are described as "modules," "engines", "models", or "generators" and such components include or take a form of a general purpose or special purpose hardware (e.g., general or special purpose processors), firmware, and/or software embodied in a non-transitory computer-readable (storage) medium for execution by one or more processors to perform described functionality.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to explain the principles of the examples, the practical application, and to enable others of ordinary skill in the art to understand the disclosure for various examples with various modifications as are suited to the particular use contemplated.

Different examples of the system(s), device(s), and method(s) disclosed herein include a variety of components, features, and functionalities. It should be understood that the various examples of the system(s), device(s), and method(s) disclosed herein may include any of the components, features, and functionalities of any of the other examples of the system(s), device(s), and method(s) disclosed herein in any combination or any sub-combination, and all of such possibilities are intended to be within the scope of the disclosure.

Thus, examples of the present disclosure relate to enumerated clauses (ECs) listed below in any combination or any sub-combination.

EC 1 is a computer-implemented method for providing diagnosis assistance, the method comprising: receiving, at a server and from a remote computing device, initial data associated with a diagnostic test result of a subject, the initial data comprising one or more undetermined outliers; selecting, by the server and from among a plurality of machine-learning logic, a machine-learning logic for execution based on a type of the diagnostic test result; determining, by the server executing the machine-learning logic and based on the initial data, a similarity between the initial data and diagnostic test result data stored in a database, wherein the machine-learning logic is trained using diagnostic training data including test results and imaging labeled as known outliers; based on the similarity between the initial data and the diagnostic test result data being within a similarity threshold, providing an inquiry for display at the remote computing device to solicit additional information useful to resolve the one or more undetermined outliers; receiving input data from the remote computing device in response to the inquiry; and storing the input data in the database.

EC 2 is the method of EC 1, wherein: said receiving the initial data associated with the diagnostic test result of the subject comprises receiving imaging data of the subject, and wherein said providing the inquiry for display comprises providing the inquiry requesting additional subject data about the subject including one or more of a breed, an age, and information related to any medication taken.

EC 3 is the method of any of ECs 1-2, further comprising: based on receiving a threshold number of additional subject data from a plurality of subjects and generating a confirmed diagnosis due to analysis of the threshold number of additional subject data, tuning the machine-learning logic and the similarity threshold.

EC 4 is the method of any of ECs 1-3, wherein: said receiving the initial data associated with the diagnostic test result of the subject comprises receiving flow cytometry data, and wherein said providing the inquiry for display comprises providing the inquiry requesting that an aliquot of a sample of the subject be sent to a lab for testing.

EC 5 is the method of any of ECs 1-4, further comprising based on receiving a threshold number of samples from a plurality of subjects and generating a confirmed diagnosis due to analysis of the threshold number of samples, tuning the machine-learning logic and the similarity threshold.

EC 6 is the method of any of ECs 1-5, wherein: said receiving the initial data associated with the diagnostic test result of the subject comprises receiving flow cytometry data from an analyzer machine, and wherein said providing the inquiry for display comprises providing the inquiry requesting additional hardware data about the analyzer machine or about operating conditions of the analyzer machine to solicit additional information useful to determine whether any abnormality is due to operation of the analyzer machine or due to a morphology of the diagnostic test result.

EC 7 is the method of any of ECs 1-6, wherein said receiving the initial data associated with the diagnostic test result of the subject comprises receiving images from an imaging system, and wherein said providing the inquiry for display comprises providing the inquiry requesting testing for histology, immunohistochemistry, or immunocytochemistry.

EC 8 is the method of any of ECs 1-7, wherein: said receiving the initial data associated with the diagnostic test result of the subject comprises receiving urinalysis test result data, and wherein said providing the inquiry for display comprises providing the inquiry requesting information related to how a urine sample was collected.

EC 9 is the method of any of ECs 1-8, wherein: said determining the similarity between the initial data and the diagnostic test result data stored in the database comprises: determining a set of hematological data examples being closest matches to the initial data, wherein a number of examples within the set of hematological data examples has a preset maximum.

EC 10 is the method of any of ECs 1-9, further comprising: selecting a plurality of inquiries for display mapping to the set of hematological data examples, wherein the inquiry for display is one of the plurality of inquiries for display.

EC 11 is the method of any of ECs 1-10, wherein: said providing the inquiry for display comprises providing the inquiry for display in substantially real-time upon generation and transmission of the diagnostic test result of the subject to the server.

EC 12 is the method of any of ECs 1-11, wherein: the database is a referential database, and the method further comprises: storing metadata that identifies the initial data along with the input data to catalog results.

EC 13 is the method of any of ECs 1-12, wherein: the database stores inquiry and similarity threshold pairings, and the method further comprises: selecting from the database, the inquiry for display based on the similarity threshold.

EC 14 is the method of any of ECs 1-13, wherein: the initial data associated with the diagnostic test result of a subject includes one or more of a species, an age, and a weight, of the subject as well as a test result from a hematology analyzer, and wherein said determining the similarity between the initial data and the diagnostic test result data stored in the database, comprises determining the similarity between the initial data and the diagnostic test result data stored in the database from subjects of a same species and having age and weight within a preset range.

EC 15 is the method of any of ECs 1-14, further comprising displaying a dot plot of the initial data at the server.

EC 16 is a server comprising: one or more processors; and non-transitory computer readable medium having stored therein instructions that when executed by the one or more processors, causes the server to perform functions comprising: receiving, from a remote computing device, initial data associated with a diagnostic test result of a subject, the initial data comprising one or more undetermined outliers; selecting, from among a plurality of machine-learning logic, a machine-learning logic for execution based on a type of the diagnostic test result; determining, by executing the machine-learning logic and based on the initial data, a similarity between the initial data and diagnostic test result data stored in a database, wherein the machine-learning logic is trained using diagnostic training data including test results and imaging labeled as known outliers; based on the similarity between the initial data and the diagnostic test result data being within a similarity threshold, providing an inquiry for display at the remote computing device to solicit additional information useful to resolve the one or more undetermined outliers; receiving input data from the remote computing device in response to the inquiry; and storing the input data in the database.

EC 17 is the server of EC 16, wherein: said receiving the initial data associated with the diagnostic test result of the subject comprises receiving imaging data of the subject, and wherein said providing the inquiry for display comprises providing the inquiry requesting additional subject data about the subject including one or more of a breed, an age, and information related to any medication taken.

EC 18 is the server of any of ECs 16-17, wherein: said receiving the initial data associated with the diagnostic test result of the subject comprises receiving flow cytometry data, and wherein said providing the inquiry for display comprises providing the inquiry requesting that an aliquot of a sample of the subject be sent to a lab for testing.

EC 19 is the server of any of ECs 16-18, wherein: said receiving the initial data associated with the diagnostic test result of the subject comprises receiving flow cytometry data from an analyzer machine, and wherein said providing the inquiry for display comprises providing the inquiry requesting additional hardware data about the analyzer machine or about operating conditions of the analyzer machine to solicit additional information useful to determine whether any abnormality is due to operation of the analyzer machine or due to a morphology of the diagnostic test result.

EC 20 is a non-transitory computer readable medium having stored thereon instructions, that when executed by one or more processors of a computing device, cause the computing device to perform functions comprising: receiving, from a remote computing device, initial data associated with a diagnostic test result of a subject, the initial data comprising one or more undetermined outliers; selecting, from among a plurality of machine-learning logic, a machine-learning logic for execution based on a type of the diagnostic test result; determining, by executing the machine-learning logic and based on the initial data, a similarity between the initial data and diagnostic test result data stored in a database, wherein the machine-learning logic is trained using diagnostic training data including test results and imaging labeled as known outliers; based on the similarity between the initial data and the diagnostic test result data being within a similarity threshold, providing an inquiry for display at the remote computing device to solicit additional information useful to resolve the one or more undetermined outliers; receiving input data from the remote computing device in response to the inquiry; and storing the input data in the database.

EC 21 is the non-transitory computer readable medium of EC 20, wherein the initial data associated with the diagnostic test result of a subject includes one or more of a species, an age, and a weight, of the subject as well as a test result from a hematology analyzer, and wherein said determining the similarity between the initial data and the diagnostic test result data stored in the database, comprises determining the similarity between the initial data and the diagnostic test result data stored in the database from subjects of a same species and having age and weight within a preset range.

By the term "substantially" and "about" used herein, it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide. The terms "substantially" and "about" represent the inherent degree of uncertainty that may be attributed to any quantitative comparison, value, measurement, or other representation. The terms "substantially" and "about" are also utilized herein to represent the degree by which a quantitative representation may vary from a stated reference without resulting in a change in the basic function of the subject matter at issue.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A computer-implemented method for providing diagnosis assistance, the method comprising:

receiving, at a server and from a remote computing device, initial data associated with a diagnostic test result of a subject, and a similarity number, the initial data comprising one or more undetermined outliers;

selecting, by the server and from among a plurality of machine-learning logic, a machine-learning logic for execution based on a type of the diagnostic test result;

determining, by the server executing the machine-learning logic and based on the initial data, a similarity metric comprising a vector distance between the initial data and diagnostic test result data stored in a database, wherein the machine-learning logic is trained using diagnostic training data including test results and imaging labeled as known outliers;

selecting, from the diagnostic test result data based on the similarity metric, a plurality of test results, wherein the number of test results included in the plurality of test results equals the similarity number;

determining, by the machine-learning logic, a similarity threshold, based on an analysis of the plurality of test results, the similarity threshold comprising a value for the similarity metric;

based on the similarity metric between the initial data and the diagnostic test result data being within the similarity threshold, providing an inquiry for display at the remote computing device to solicit additional information useful to resolve the one or more undetermined outliers;

receiving input data from the remote computing device in response to the inquiry; and storing the input data in the database.

2. The computer-implemented method of claim 1, wherein said receiving the initial data associated with the diagnostic test result of the subject comprises receiving imaging data of the subject, and wherein said providing the inquiry for display comprises providing the inquiry requesting additional subject data about the subject including one or more of a breed, an age, and information related to any medication taken.

3. The computer-implemented method of claim 2, further comprising:

based on receiving a threshold number of additional subject data from a plurality of subjects and generating a confirmed diagnosis due to analysis of the threshold number of additional subject data, tuning the machine-learning logic and the similarity threshold.

4. The computer-implemented method of claim 1, wherein said receiving the initial data associated with the diagnostic test result of the subject comprises receiving flow cytometry data, and wherein said providing the inquiry for display comprises providing the inquiry requesting that an aliquot of a sample of the subject be sent to a lab for testing.

5. The computer-implemented method of claim 4, further comprising:

based on receiving a threshold number of samples from a plurality of subjects and generating a confirmed diagnosis due to analysis of the threshold number of samples, tuning the machine-learning logic and the similarity threshold.

6. The computer-implemented method of claim 1, wherein said receiving the initial data associated with the diagnostic test result of the subject comprises receiving flow cytometry data from an analyzer machine, and wherein said providing the inquiry for display comprises providing the inquiry requesting additional hardware data about the analyzer machine or about operating conditions of the analyzer machine to solicit additional information useful to determine whether any abnormality is due to operation of the analyzer machine or due to a morphology of the diagnostic test result.

7. The computer-implemented method of claim 1, wherein said receiving the initial data associated with the diagnostic test result of the subject comprises receiving images from an imaging system, and wherein said providing the inquiry for display comprises providing the inquiry requesting testing for histology, immunohistochemistry, or immunocytochemistry.

8. The computer-implemented method of claim 1, wherein said receiving the initial data associated with the diagnostic test result of the subject comprises receiving urinalysis test result data, and wherein said providing the inquiry for display comprises providing the inquiry requesting information related to how a urine sample was collected.

9. The computer-implemented method of claim 1, wherein said determining the similarity between the initial data and the diagnostic test result data stored in the database comprises:

determining a set of hematological data examples being closest matches to the initial data, wherein a number of examples within the set of hematological data examples has a preset maximum.

10. The computer-implemented method of claim 9, further comprising:

selecting a plurality of inquiries for display mapping to the set of hematological data examples, wherein the inquiry for display is one of the plurality of inquiries for display.

11. The computer-implemented method of claim 1, wherein said providing the inquiry for display comprises providing the inquiry for display in substantially real-time upon generation and transmission of the diagnostic test result of the subject to the server.

12. The computer-implemented method of claim 1, wherein the database is a referential database, and the method further comprises:

storing metadata that identifies the initial data along with the input data to catalog results.

13. The computer-implemented method of claim 1, wherein the database stores inquiry and similarity threshold pairings, and the method further comprises:
    selecting from the database, the inquiry for display based on the similarity threshold.

14. The computer-implemented method of claim 1, wherein the initial data associated with the diagnostic test result of a subject includes one or more of a species, an age, and a weight, of the subject as well as a test result from a hematology analyzer, and
    wherein said determining the similarity between the initial data and the diagnostic test result data stored in the database, comprises determining the similarity between the initial data and the diagnostic test result data stored in the database from subjects of a same species and having age and weight within a preset range.

15. The computer-implemented method of claim 1, further comprising displaying a dot plot of the initial data at the server.

16. A server comprising:
    one or more processors; and
    non-transitory computer readable medium having stored therein instructions that when executed by the one or more processors, causes the server to perform functions comprising:
        receiving, from a remote computing device, initial data associated with a diagnostic test result of a subject, and a similarity number, the initial data comprising one or more undetermined outliers;
        selecting, from among a plurality of machine-learning logic, a machine-learning logic for execution based on a type of the diagnostic test result;
    determining, by executing the machine-learning logic and based on the initial data, a similarity metric comprising a vector distance between the initial data and diagnostic test result data stored in a database, wherein the machine-learning logic is trained using diagnostic training data including test results and imaging labeled as known outliers;
        selecting, from the diagnostic test result data based on the similarity metric, a plurality of test results, wherein the number of test results included in the plurality of test results equals the similarity number;
        determining, by the machine-learning logic, a similarity threshold, based on an analysis of the plurality of test results, the similarity threshold comprising a value for the similarity metric;
        based on the similarity metric between the initial data and the diagnostic test result data being within the similarity threshold, providing an inquiry for display at the remote computing device to solicit additional information useful to resolve the one or more undetermined outliers;
        receiving input data from the remote computing device in response to the inquiry; and
        storing the input data in the database.

17. The server of claim 16, wherein said receiving the initial data associated with the diagnostic test result of the subject comprises receiving imaging data of the subject, and
    wherein said providing the inquiry for display comprises providing the inquiry requesting additional subject data about the subject including one or more of a breed, an age, and information related to any medication taken.

18. The server of claim 16, wherein said receiving the initial data associated with the diagnostic test result of the subject comprises receiving flow cytometry data, and
    wherein said providing the inquiry for display comprises providing the inquiry requesting that an aliquot of a sample of the subject be sent to a lab for testing.

19. The server of claim 16, wherein said receiving the initial data associated with the diagnostic test result of the subject comprises receiving flow cytometry data from an analyzer machine, and
    wherein said providing the inquiry for display comprises providing the inquiry requesting additional hardware data about the analyzer machine or about operating conditions of the analyzer machine to solicit additional information useful to determine whether any abnormality is due to operation of the analyzer machine or due to a morphology of the diagnostic test result.

20. A non-transitory computer readable medium having stored thereon instructions, that when executed by one or more processors of a computing device, cause the computing device to perform functions comprising:
    receiving, from a remote computing device, initial data associated with a diagnostic test result of a subject, and a similarity number, the initial data comprising one or more undetermined outliers;
    selecting, from among a plurality of machine-learning logic, a machine-learning logic for execution based on a type of the diagnostic test result;
    determining, by executing the machine-learning logic and based on the initial data, a similarity metric comprising a vector distance between the initial data and diagnostic test result data stored in a database, wherein the machine-learning logic is trained using diagnostic training data including test results and imaging labeled as known outliers;
    selecting, from the diagnostic test result data based on the similarity metric, a plurality of test results, wherein the number of test results included in the plurality of test results equals the similarity number;
    determining, by the machine-learning logic, a similarity threshold, based on an analysis of the plurality of test results, the similarity threshold comprising a value for the similarity metric;
    based on the similarity metric between the initial data and the diagnostic test result data being within the similarity threshold, providing an inquiry for display at the remote computing device to solicit additional information useful to resolve the one or more undetermined outliers;
    receiving input data from the remote computing device in response to the inquiry; and
    storing the input data in the database.

21. The non-transitory computer readable medium of claim 20, wherein the initial data associated with the diagnostic test result of a subject includes one or more of a species, an age, and a weight, of the subject as well as a test result from a hematology analyzer, and
    wherein said determining the similarity between the initial data and the diagnostic test result data stored in the database, comprises determining the similarity between the initial data and the diagnostic test result data stored in the database from subjects of a same species and having age and weight within a preset range.

* * * * *